United States Patent [19]

Kameyama et al.

[11] Patent Number: 4,703,061
[45] Date of Patent: Oct. 27, 1987

[54] GAMMA-AMINOBUTYRIC ACID DERIVATIVES, PROCESS FOR PRODUCTION THEREOF, AND USE THEREOF AS MEDICAMENTS

[75] Inventors: Tsutomu Kameyama, Nagoya; Jiro Kitamura, Gifu; Tetsuo Takigawa; Masao Mizuno, both of Kurashiki, all of Japan

[73] Assignee: Kuraray Co., Ltd., Okayama, Japan

[21] Appl. No.: 753,613

[22] Filed: Jul. 9, 1985

[30] Foreign Application Priority Data

Jul. 13, 1984 [JP] Japan ................................. 59-146553

[51] Int. Cl.$^4$ ..................... C07C 103/48; A61K 31/22
[52] U.S. Cl. .................................. 514/551; 514/554; 514/563; 560/170; 562/567; 260/501.11
[58] Field of Search ........................ 560/170; 562/567; 514/551, 563, 554

[56] References Cited

U.S. PATENT DOCUMENTS

| | | | |
|---|---|---|---|
| 2,234,680 | 3/1941 | Moore | 562/569 |
| 2,271,872 | 2/1942 | Mitchell | 562/567 |
| 2,414,682 | 1/1947 | Williams | 562/567 |
| 2,442,143 | 5/1948 | Pickel | 562/569 |
| 2,848,489 | 8/1958 | Kagan | 562/569 |
| 2,856,421 | 10/1958 | Hasbrouck | 562/567 |

FOREIGN PATENT DOCUMENTS

| | | | |
|---|---|---|---|
| 41734 | 4/1964 | Japan | 562/567 |
| 55-17329 | 2/1980 | Japan | 514/563 |
| 553317 | 5/1943 | United Kingdom | 562/569 |
| 561877 | 6/1944 | United Kingdom | 562/569 |

OTHER PUBLICATIONS

Burger, "Medical Chemistry," Part II, 3rd Ed., pp. 1196–1197 & 1222–1227 (1970).

*Primary Examiner*—Michael L. Shippen
*Attorney, Agent, or Firm*—Wenderoth, Lind & Ponack

[57] ABSTRACT

A compound which is 4-(3,5-dihydroxy-3-methylpentylamide)butyric acid or its pharmaceutically acceptable salt or ester; this compound being produced by reacting a salt or an ester of gamma-aminobutyric acid with beta-hydroxy-beta-methyl-delta-valerolactone, and as required, converting the resulting compound in the form of a salt or ester to a free acid, or as required, converting the resulting compound in the form of a free acid to its pharmaceutically acceptable salt or ester; and useful as a medicament for preventing or treating an impediment in cerebral function.

3 Claims, No Drawings

GAMMA-AMINOBUTYRIC ACID DERIVATIVES, PROCESS FOR PRODUCTION THEREOF, AND USE THEREOF AS MEDICAMENTS

This invention relates to novel gamma-aminobutyric acid derivatives, a process for production thereof, and the use thereof as medicaments, particularly as medicaments for preventing or treating some kind of cerebral dysfunction.

It has already been known that gamma-aminobutyric acid (GABA) performs an important function as a chemical transmitter in the brain, and participates in the regulation of metabolism in the brain [G. B. Makara et al., Neuroendocrinology, 16, 178 (1975)]. With interest in the participation of gamma-aminobutyric acid in the regulation of metabolism in the brain, a great deal of studies on the use of gamma-aminobutyric acid as a medicine have been actively conducted in recent years. Since, however, gamma-aminobutyric acid itself hardly transmigrates through the blood brain barrier and is easily excreted into urine, the prior studies have been directed mainly to the chemical modification of gamma-aminobutyric acid into a form which can easily transmigrate through the blood brain barrier, namely to the discovery of a "prodrug" of gamma-aminobutyric acid which can easily transmigrate through the blood brain barrier. For example, it has been proposed to use 4-(2,4-dihydroxy-3,3-dimethylbutylamide) butyric acid (common name, "hopantenic acid") or its pharmaceutically acceptable salts for the treatment of dementia attributed to head injuries, a surgical operation on the brain, or cerebrovascular impediments (Japanese Laid-Open Patent Publication No. 17329/1980). It has also been reported that intraperitoneal administration of nicotinoyl gamma-aminobutyric acid or isonicotinoyl gamma-aminobutyric acid to mice resulted in a marked prolongation of the sleeping time and an appearance of mild anticonvulsive activity [Summaries of Papers Presented in the 104th Annual Meeting of the Pharmaceutical Society of Japan, page 666 (1984)].

Many compounds have been studied heretofore in order to develope prodrugs for gamma-aminobutyric acid and utilize its metabolism regulating effect in the brain, but except for a few such as hopantenic acid or its salts, they have proved to be unsatisfactory in regard to toxicity or the ability to transmigrate through the brain barrier, and have not gained practical acceptance.

It is an object of this invention to provide novel and useful gamma-aminobutyric acid derivatives, particularly gamma-aminobutyric acid derivatives, which easily transmigrate through the brain barrier and exhibit a useful pharmacological action, such as the activity of improving cerebral function.

Another object of this invention is to provide a process for producing the aforesaid novel gamma-aminobutyric acid derivatives.

Still another object of this invention is to provide an agent for improving cerebral function comprising the aforesaid gamma-aminobutyric acid derivatives as an active ingredient.

Other objects and advantages of this invention will become apparent from the following detailed description.

According to one aspect of this invention, there are provided 4-(3,5-dihydroxy-3-methyl-pentylamide) butyric acid, represented by the following formula,

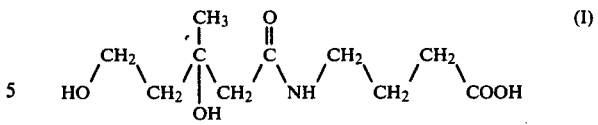

and its pharmaceutically acceptable salts and esters.

4-(3,5-Dihydroxy-3-methylpentylamide) butyric acid (to be abbreviated as "MV-GABA" for simplification) includes a DL-, a D-, and an L-form. Examples of suitable pharmaceutically acceptable salts of MV-GABA are alkali metal salts such as sodium and potassium salts, alkaline earth metal salts such as calcium, magnesium and barium salts, an ammonium salt, and organic amine salts such as trimethylamine and triethylamine salts. Of these, the calcium salt is preferred.

The pharmaceutically acceptable esters of MV-GABA include those of the type which can be easily split off by the esterase existing in the human body, and specific examples are lower alkyl esters such as methyl, ethyl, propyl, isopropyl, butyl and tert.-butyl esters.

The term "lower", as used herein means that a group or compound qualified by this term has not more than 6, preferably not more than 4, carbon atoms.

According to another aspect of this invention, the MV-GABA or its salt or ester is produced by reacting a salt or ester of gamma-aminobutyric acid with betahydroxy-beta-methyl-delta-valerolactone, and as required, converting the product in the form of a salt or ester to its free acid, i.e., MV-GABA, or as required, converting MV-GABA in the form of a free acid to its pharmaceutically acceptable salt or ester.

The reaction of the salt or ester of gamma-aminobutyric acid with the beta-hydroxy-beta-methyl-delta-valerolactone can be carried out usually in a suitable solvent at a temperature between about +30° C. and about 100° C., preferably between room temperature and about 80° C. This reaction gives a salt or ester of MV-GABA. Examples of the solvent that can be used in this reaction are water, lower alkanols such as methanol, ethanol and isopropanol, ethylene glycol, 2-methoxyethanol, and 2-ethoxyethanol, and mixtures thereof. Water, ethanol, 2-methoxyethanol, 2-ethoxyethanol and mixtures thereof are advantageously used.

The proportion of beta-hydroxy-beta-methyl-delta-valerolactone is not critical and can be varied within a wide range. For example, it is suitably used in a proportion of generally 0.5 to 5 moles, preferably 0.8 to 2 moles, per mole of the salt or ester of gamma-aminobutyric acid. More preferably, the salt or ester of gamma-aminobutyric acid and beta-hydroxy-beta-methyl-delta valerolactone are used in a mole ratio of 1.1 and the reaction is carried out until it is fully completed, because this eases the purification of the product after the reaction.

The salt of gamma-aminobutyric acid that can be used as a starting material in the above reaction includes, for example, alkali metal salts such as sodium and potassium salts; alkaline earth metal salts such as calcium, magnesium and barium salts; an ammonium salt; and organic amine salts such as trimethylamine and triethylamine salts. The esters of gamma-aminobutyric acid include lower alkyl esters such as methyl, ethyl, propyl, isopropyl, butyl and tert-butyl esters. It is particularly convenient to use calcium gamma-aminobutyrate as the starting material and react it with beta-hydroxy-beta-methyl-delta-valerolactone.

As required, a salt or an ester of MV-GABA obtained by the above reaction can be converted to its free acid, i.e. MV-GABA by the methods known per se, for example, by treatment with a strong acid-type cation exchange resin or by hydrolysis respectively. The free acid may be further converted to a pharmaceutically acceptable salt or ester.

The MV-GABA and its pharmaceutically acceptable salts or esters provided by this invention easily transmigrate through the blood brain barrier, and have marked effects on the regulation of metabolism in the brain. The following animal experiments demonstrate that, for example, these compounds provided by this invention show an action of markedly decreasing locomotor activity, and antagonistic effect against the increase of motor activity induced by methamphetamine, an action of markedly prolonging the time of sleeping induced by pentobarbital, an action of markedly inhibiting the increase of motor activity induced by atropine, and an effect of significantly improving the memories of a cycloheximide-induced amnesia model and an electric convulsive shock-induced amnesia model.

The following pharmacological tests were conducted in order to demonstrate that the compounds provided by this invention have excellent pharmacological characteristics.

PHARMACOLOGICAL TESTS

In Tests 1 to 4 given below, ddY-strain male mice (body weight 20–25 g) were used, and the experiments were carried out in a semi-soundproof, constant-temperature room kept at a temperature of 23±1° C. and a humidity of 55±2%. The mice were allowed to take feed and water freely.

Test 1: Effects on locomotor activity (1) Wheel cage method

The effects of the test compound on the locomotor activities of the mice were examined by using wheel cages (made by Kishimoto Ika). Before the experiment, the mice were put in cages, and those mice which showed a rotating speed of 200 to 300 revolutions per 15 minutes were selected and used in the experiment. The mice were used in groups each consisting of 8 mice. The test compound was intraperitoneally administered to the mice in the doses indicated, and immediately then, the mice were put into the cages. The locomotor activities (the number of revolutions) were measured for 90 minutes at 15 minute intervals, and compared with that of the control group. The results are shown in Table 1.

TABLE 1

| Test compound | Dose (mg/kg) i.p. | Motor activity (total number of revolutions per mouse) Time elapsed after administration (minutes) | | | | | |
|---|---|---|---|---|---|---|---|
| | | 15 | 30 | 45 | 60 | 75 | 90 |
| Control | — | 222 | 438 | 635 | 792 | 989 | 1180 |
| MV-GABA-Ca salt (*) | 250 | 201 | 406 | 560 | 727 | 865 | 916 |
| MV-GABA-Ca salt (*) | 500 | 132 | 289 | 448 | 615 | 826 | 1034 |
| MV-GABA-Ca salt (*) | 1000 | 76 | 165 | 265 | 428 | 639 | 837 |

(*): Calcium 4-(3,5-dihydroxy-3-methylpentylamide)-butyrate (the same hereinafter)

(2) Automex method

The effects of the test compound on planar locomotor activity of the mice were examined by using an automex activity meter (made by Columbus Company). Mice which showed a rotating speed of 200 to 300 revolutions per 15 minutes in the wheel cages in section (1) above were selected and divided into 5-membered groups. The test compound was intraperitoneally administered to the mice in doses indicated. Immediately then, five mice were put into each of transparent plastic cages (27×17×17 cm), and placed on the automex activity meter. The motor activity for 30 minutes was measured at 5 minutes intervals, and compared with that of the control group. The results are shown in Table 2.

TABLE 2

| Test compound | Dose (mg/kg) i.p. | Motor activity (total number of counts) Time elapsed after administration (minutes) | | | | | |
|---|---|---|---|---|---|---|---|
| | | 5 | 10 | 15 | 20 | 25 | 30 |
| Control | — | 251 | 377 | 471 | 509 | 544 | 558 |
| MV-GABA-Ca salt | 500 | 172 | 241 | 307 | 405 | 505 | 558 |
| MV-GABA-Ca salt | 1000 | 91 | 128 | 156 | 177 | 189 | 203 |

Test 2: Antagonistic effect against methamphetamine (automex method)

Mice were used in 5-membered groups. Each of the test compounds was intraperitoneally administered to the mice in a predetermined dose, and immediately then, the mice were subcutaneously injected with methamphetamine in a dose of 3 mg/kg. The action of the test compounds on motor activity enhanced by methamphetamine was examined in accordance with the automex method given above. The results are shown in Table 3.

TABLE 3

| Test compound | Dose (mg/kg) i.p. | Motor activity (total number of counts) Time elapsed after administration (minutes) | | | | | |
|---|---|---|---|---|---|---|---|
| | | 5 | 10 | 15 | 20 | 25 | 30 |
| Control I (*1) | — | 50 | 67 | 80 | 86 | 88 | 126 |
| Control II (*2) | — | 26 | 60 | 131 | 211 | 322 | 424 |
| MV-GABA Ca salt | 500 | 10 | 11 | 22 | 38 | 71 | 126 |
| Ca salt of hopantenic acid | 500 | 26 | 55 | 94 | 144 | 273 | 408 |

(*1): In place of the test compound and methamphetamine, normal saline solution was administered.
(*2): Normal saline solution was intraperitoneally administered instead of the test compound, and immediately then, methamphetamine (3 mg/kg) was subcutaneously injected.

It is obvious from Table 3 that when calcium hopantenate was administered in a dose of 500 mg/kg, its antagonistic effect against the increase of motor activity induced by methamphetamine was scarcely observed, but the administration of MV-GABA-Ca salt in a dose of 500 mg/kg markedly inhibited the motor activity of mice enhanced by methamphetamine.

Test 3: Effect of prolonging the time of sleeping induced by pentobarbital

The effects of the test compounds on sleeping induced by pentobarbital were examined. The disappearance of righting reflex for 5 seconds or more was used as an index of sleeping. Mice were divided into 10-membered groups. Each of the test compounds was intraperitoneally administered to the mice in the doses indicated. Immediately then, pentobarbital sodium salt was subcutaneously injected into the mice in a dose of 50 mg/kg, and the sleeping time was compared with that of a group to which pentobarbital alone was injected (control). The results are shown in Table 4.

TABLE 4

| Test compound | Dose (mg/kg) i.p. | Sleeping time (minutes) |
| --- | --- | --- |
| Control | — | 43.5 ± 2.8 |
| MV-GABA-Ca salt | 1000 | 62.7 ± 7.5 |
| MV-GABA-Ca salt | 2000 | 77.2 ± 5.2 |
| Ca hopantenate | 1000 | 57.0 ± 6.7 |
| Ca hopantenate | 2000 | 67.0 ± 5.9 |

Test 4: Antagonistic effect against atropine (automex method)

Each of the test compounds was intraperitoneally administered to mice divided into 6-membered groups, and immediately then, atropine was subcutaneously injected into the mice in a dose of 30 mg/kg. The effect of each test compound on the enhancement of motor activity induced by atropine was examined in accordance with the automex method. The results are shown in Table 5.

TABLE 5

| Test compound | Dose (mg/kg) i.p. | Motor activity (total number of counts) Time elapsed after administration (minutes) | | | | | |
| --- | --- | --- | --- | --- | --- | --- | --- |
| | | 5 | 10 | 15 | 20 | 25 | 30 |
| Control (Normal saline solution) | — | 50 | 67 | 80 | 86 | 88 | 126 |
| Atropine | 30 | 59 | 233 | 425 | 620 | 806 | 964 |
| MV-GABA Ca salt | 600 + At (30) | 8 | 12 | 19 | 27 | 47 | 92 |
| Ca salt of hopantenic acid | 600 + At (30) | 16 | 16 | 29 | 56 | 88 | 151 |

Test 5: Effect of improving the memories of amnesia models

1. Test animals

The test animals used were ddY-strain male mice (body weight 30–35 g). The experiment was carried out indoors at about 20° C., and the mice were allowed to take feed and water freely. 2. Effects on memorized behaviors (1) Experimental device A device comprised of a floor grid surrounded on four sides by acrylic glass walls each having a lateral dimension of 21 cm and a wooden platform, 4×4×4 cm in size, fixed centrally to the floor grid was placed in a wooden semi-soundproof box having a size of 21×21×40 cm with a 15W electric bulb suspended from its ceiling.

The floor grid consisted of stainless steel rods, 3 mm in diameter, arranged at intervals of 8 mm. An intermittent electric shock (1 Hz, 0.5 sec., 60 V DC) was applied to the grid by an electric impulse apparatus and an isolator.

(2) Training test

A mouse was placed in a predetermined direction on the platform. Immediately after the mouse stepped down onto the floor grid (when the mouse's four limbs left the platform), an electric shock was applied to the floor grid, and the intermittent application of the electric shock was continued until the mouse climbed up the platform to escape from the electric shock. The time which elapsed until the mouse stepped down from the platform (SDL, step down latency) and the time which elapsed until the mouse escaped to the platform from the electric shock (ELL, escape learning latency) were measured.

The above experiment was conducted on a number of mice, and those mice which showed SDL and ELL values within certain specified ranges were selected, and used in the following tests.

(3) Retention test

By the same procedure as in the training test, a mouse was placed on the platform, and its step down latency (SDL) was measured. The cut-off time was 300 seconds.

After the mouse stepped down, or the cut-off time elapsed, the mouse was placed on the floor grid at a corner of the device with its head directed in a direction opposite to the platform. An electric shock was applied to the mouse and its escape learning latency (ELL) was measured.

3. Preparation of amnesia-induced animals (1) Cycloheximide (to be abbreviated "CXM")—induced amnesia Mice divided into groups each consisting of not less than 20 mice were subjected to the training test, and immediately then subcutaneously injected with CXM (150 mg/kg). Twenty-four hours later, the mice was subjected to the retention test.

(2) Electric convulsive shock (to be abbreviated "ECS")-induced amnesia

Mice divided into groups each consisting of not less than 15 mice were subjected to the training test, and immediately then, ECS (300 V DC, 0.5 sec.) was applied to the mice through both ears. Twenty-four hours later, the mice were subjected to the retention test.

4. Administration of test compounds

Immediately after administration of CXM or application of ECS, a 0.9% normal saline solution of each of the test compounds was intraperitoneally administered to the mice. Separately, a 5% gum arabic solution of CXM was administered to the mice in a control group.

5. Results (1) Effects on CXM-induced amnesia

In the training test, the mice in the group not pretreated with CXM showen an almost constant SDL of 6.9 to 7.5 sec. and an almost constant ELL of 29.0 to 32.0 sec.

The trained mice were subjected to the retention test 24 hours after the training test. The results of the retention test are shown in Table 6.

TABLE 6

| Treatment | Number of mice | Dose mg/kg, i.p. | Latency (mean ± S.E.) | |
| --- | --- | --- | --- | --- |
| | | | Step-down (sec) | Escape learning (sec) |
| Control | (61) | | 263.4 ± 8.1 | 5.0 ± 0.4 |
| CXM control | (28) | | 95.2 ± 8.1* | 11.8 ± 0.8* |

TABLE 6-continued

| Treatment | Number of mice | Dose mg/kg, i.p. | Latency (mean ± S.E.) | |
|---|---|---|---|---|
| | | | Step-down (sec) | Escape learning (sec) |
| CXM-(MV-GABA-Ca) | (34) | 500 | 120.5 ± 10.6*,† | 10.5 ± 0.6* |
| | (43) | 1000 | 175.2 ± 16.1*,†† | 7.5 ± 0.6*,†† |
| MV-GABA-Ca | (20) | 1000 | 260.5 ± 14.0 | 5.2 ± 0.6 |
| CXM-HOPA | (34) | 500 | 122.3 ± 13.0* | 10.3 ± 0.7* |
| | (26) | 1000 | 187.7 ± 19.7*,†† | 8.2 ± 1.0*,†† |
| HOPA | (18) | 1000 | 275.9 ± 9.7 | 5.6 ± 0.8 |

*$p < 0.01$ vs control
†$p < 0.05$, ††$p < 0.01$ vs CXM control
**HOPA = Calcium 4-(2,4- dihydroxy-3,3-dimethyl-butylamide)butyrate (1) In the retention test, the SDL of the control group to which CXM (150 mg/kg) was administered immediately after the training test was significantly shortened, and its ELL was signigicantly prolonged as compared with the control group. Hence, the induction of amnesia was observed.

(2) The MV-GABA-Ca group and HOPA group to which CXM was not administered did not show memory activating action as compared with the control group.

(3) MV-GABA-Ca significantly improved the shortening of SDL iduced by CXM in groups to which MV-GABA-Ca was administered in doses each of 500 mg/kg and 1,000 mg/kg. Furthermore, the administration of 1,000 mg/kg of MV-GABA-Ca significantly improved the prolongation of ELL induced by CXM.

(2) Effects on ECS-induced amnesia

The test was conducted by setting the voltage of ECS at 200 V and 300 V. When ECS was applied at 200 V, tonic convulsion did not occur, and in the retention test, no amnesia action was observed. When ECS was applied at 300 V, the mice showed tonic convulsion, and their somatic reflex disappeared. But the mice recovered 1 to 2 minutes later. After 24 hours, the locomotor activities of these mice, measured by the automex method, did not show an appreciable difference from that of the control group.

Using the mice to which ECS was applied at 300 V, the effects of MV-GABA-Ca and HOPA were tested. The results are given in Table 7.

TABLE 7

| Treatment | Number of mice | Dose mg/kg, i.p. | Latency (mean ± S.E.) | |
|---|---|---|---|---|
| | | | Step-down (sec) | Escape learning (sec) |
| Control | (20) | | 250.9 ± 17.0 | 6.0 ± 0.8 |
| ECS Control | (20) | | 103.5 ± 19.8** | 12.2 ± 1.1** |
| ECS-(MV-GABA-Ca) | (20) | 250 | 104.6 ± 17.7** | 12.8 ± 1.6** |
| | (20) | 500 | 158.5 ± 21.7* | 8.0 ± 1.1† |
| | (20) | 750 | 215.2 ± 15.9 † | 6.7 ± 0.7† |

*$p < 0.05$, **$p < 0.01$ vs control
†$p < 0.01$, vs ECS control (1) In the retention test, the SDL of the group to which ECS was applied at 300 V immediately after the training test was signigicantly shortened, and its ELL was also significantly prolonged, as compared with the control group. Hence, the induction of amnesia was noted.

(2) At a dose of 750 mg/kg, MV-GABA-Ca significantly improved shortening of SDL and also the prolongation of ELL. At a dose of 500 mg/kg, MV-GABA-Ca significantly improved the prolongation of ELL.

TOXICITY TEST

Calcium 4-(3,5-dihydroxy-3-methylpentylamide) butyrate was intraperitoneally administered in doses of 500 mg/kg and 1,000 mg/kg respectively to eight ddY-strain male mice (body weight 20 to 25 g). There was no case of death, and it was judged that the $LD_{50}$ value was more than 2,000 mg/kg.

These mice were also observed for changes in behavior, nervous symptoms, autonomic nervous symptoms, and toxic symptoms in accordance with the Irwin's observation method. At doses of 1,000 mg/kg or below, no marked difference from the control group could be found.

As demonstrated by the results of the above experiments, the gamma-aminobutyric acid derivatives of this invention easily transmigrate through the blood brain barrier, and exhibit an action of markedly decreasing locomotor activity, an antagonistic effect against the increase of motor activity induced by methamphetamine, an action of markedly prolonging the time of sleeping induced by pentobarbital, an action of markedly inhibiting the increase of motor activity induced by atropine, and an effect of significantly improving the memories of a cycloheximide-induced amnesia model and an electric convulsive shock-induced amnesia model as well as low toxicity. Accordingly, they can be used as medicaments for the prevention and treatment of various impediments in cerebral function induced by derangement in the regulation of metabolism in the brain. Specifically, these compounds show an excellent efficacy in the prevention and treatment of dementia attributed to head injuries, a surgical operation on the brain, cerebrovascular impediments and the like; dementia attributed to endocrine diseases and metabolic diseases such as hyperthyroidism, hypothyroidism, hyperparathyroidism, hypoparathyroidism, Wilson disease, liver disease, hyperlipemia, hypoglycemia, hypercalcemia, hypocalcemia, Cushing syndrome, hypopituitarism and uremia; dementia attributed to hypoxia such as cardio-pulmonary diseases anemia; dementia attributed to infectious diseases such as brain abscess, bacillary meningitis, tubercular meningitis, syphilis and cerebral helminthiasis, and dementia attributed to diseases of the central nervous system, such as Alzheimer-type senile dementia, Pick disease, Huntington disease and Parkinson disease.

In using the gamma-aminobutyric acid derivatives of the invention for the prevention and treatment of impediments in cerebral function, their doses may be varied widely depending upon the purpose of administration, the route of administration, the condition, body weight, age and sex of a patient, the judgement of a physician who treats the patient, etc. Generally, in administrations to humans, the doses are 0.01 mg/kg/day to 1,000 mg/kg/day, preferably 0.1 mg/kg/day to 100 mg/kg/day, more preferably 0.2 mg/kg/day to 50 mg/kg/day, either at a time or in several divided portions daily.

The route of administration may be oral or parenteral (e.g., intravenous, intraarterial, intramuscular, intraperitoneal, intramedullary, intrarectal).

For administration, the gamma-aminobutyric acid derivatives may be formulated into forms suitable for the above routes of administration, for example forms suitable for oral administration such as tablets, granules, powders, coated tablets, hard capsules, elastic capsules and syrups, or forms suitable for injection or intravenous drip infusion such as suspensions, solutions, or oily or aqueous emulsions.

Adjuvants normally used in formulating medicaments in the above-exemplified forms may equally be used as pharmaceutically acceptable liquid or solid diluents or carriers for formulating the pharmaceutical composition or agent of this invention. Specific examples include syrup, gum arabic, gelatin, sorbitol, tragacanth, polyvinyl pyrrolidone, magnesium stearate, talc, polyethylene glycol, silica, lactose, sucrose, corn starch, calcium phosphate, glycine, potato starch, carboxymethyl cellulose calcium, sodium laurylsulfate, water, ethanol, glycerol, mannitol, and a phosphate buffer.

The pharmaceutical composition or agent of this invention may, if required, further contain other adjuvants customarily used in the field of pharmaceutical formulation, such as coloring agents, flavors, corrigents, antiseptics, dissolution aids, suspending agents and dispersing agents.

The pharmaceutical composition or agent may be in unit dosage forms such as tablets, capsules, coated tablets and ampoules mentioned above, or may be in a form contained in a multiunit dosage receptacle.

The pharmaceutical composition or agent, depending upon its form, etc., may contain the gamma-aminobutyric acid derivatives of the invention in a concentration of generally 0.01 to 50% by weight, preferably 0.1 to 20% by weight.

The following Examples illustrate the present invention more specifically.

EXAMPLE 1

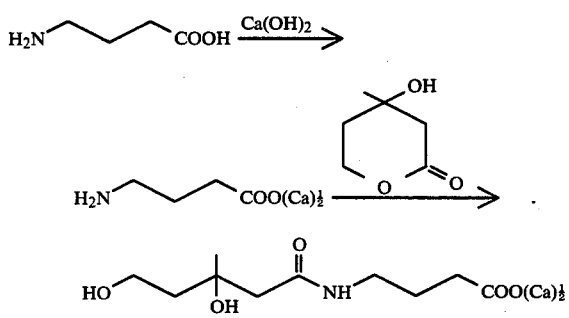

Water (10 ml) was added to 0.38 g (5 mmoles) of calcium hydroxide and 1.03 g (10 mmoles) of gamma-aminobutyric acid, and the mixture was stirred until the crystals dissolved. A slightly turbid white solution was obtained. By decantation, the supernatant was separated, and water was evaporated from the supernatant under reduced pressure. To the residue were added 8 ml of 2-methoxyethanol and 1.3 g (10 mmoles) of beta-hydroxy-beta-methyl-delta-valerolactone. The mixture was stirred under heating to form a uniform solution. The solution was left to stand at room temperature (about 18° C.) for 1 hour, and then heated to 110° C. under a reduced pressure of 0.3 mmHg to remove the solvent. As a result, 2.41 g of a pale yellow soft solid was obtained. The product was analyzed by a device comprised of two columns (GL-A130 and GL-A120 made by Hitachi Chemical Co., Ltd.; each having a diameter of 8 mm and a length of 50 cm) for gel-permeation chromatography (to be abbreviated "GPC") connected in series using tetrahydrofuran as a developing solvent and a differential refractometer as a detector. It was determined that the product contained more than 90% by weight of a component corresponding to a molecular weight of about 240 when calibrated by using n-alcohols.

An aliquot of the above component was purified by using the same GPC device, and analyzed by NMR spectroscopy, infrared spectroscopy and elemental analysis. By these analyses, the above component was determined to be calcium 4-(3,5-dihydroxy-3-methylpentylamide) butyrate.

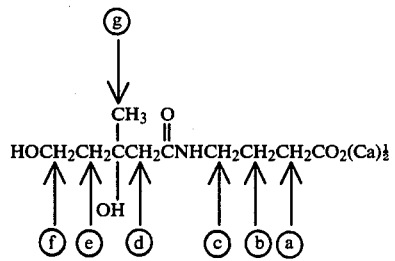

IR (cm$^{-1}$): 3300 (—OH), 1720 ( $\diagdown$C=O), 1640 (—C(=O)—NH—), 1560 ( $\diagdown$NH of amide group)

Elemental analysis.
Found (%): C, 44.01; H, 6.79.
Calculated (%): C, 44.10; H, 6.66.

EXAMPLE 2

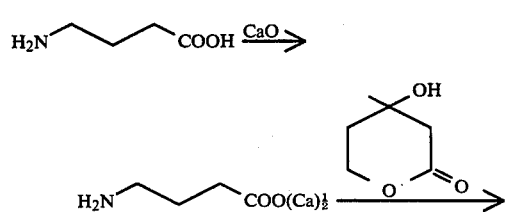

-continued

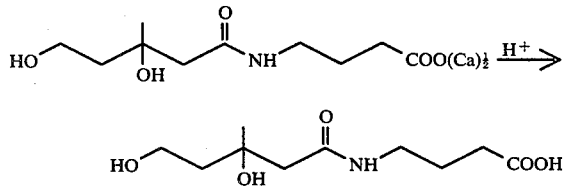

Calcium oxide (0.28 g; 5 mmoles) and 1.03 g (10 mmoles) of gamma-aminobutyric acid were added to 5 ml of ethanol, and the mixture was stirred under reflux for 5 hours. On cooling, a white powder was precipitated. By decantation, the supernatant was taken into an eggplant-shaped flask, and 1.3 g (10 mmoles) of beta-hydroxy-beta-methyl-delta-valerolactone was added. The mixture was stirred at room temperature (about 15° C.) for 12 hours. Ethanol was distilled off under reduced pressure to give 2.18 g of a slightly yellow soft solid. Analysis of this product by NMR spectroscopy in D$_2$O led to the determination that it was calcium 4-(3,5-dihydroxy-3-methylpentylamide) butyrate having a purity of more than 95% containing small amounts of gamma-aminobutyric acid, beta-hydroxy-beta-methyl-delta-valerolactone and ethanol. This product was dissolved in 5 ml of ethanol and then 50 ml of diethyl ether was gradually added to this solution with vigorous stirring to give a slightly yellowish white precipitate. The precipitate (powder) was collected by filtration and found to be almost pure by NMR analysis.

The powder was then dissolved in 50 ml of distilled water and the solution was passed at room temperature through a column packed with a strong acid-type cation exchange resin (Dowex 50W×8, a product of Dow Chemical Co.) to convert it to 4-(3,5-dihydroxy-3-methyl-pentylamide) butyric acid. The results of NMR analysis of this compound were substantially the same as those obtained in Example 1. The results of its elemental analysis were as follows:
Found (%): C, 51.09; H, 8.51.
Calculated (%): C, 51.47; H, 8.21.

EXAMPLE 3

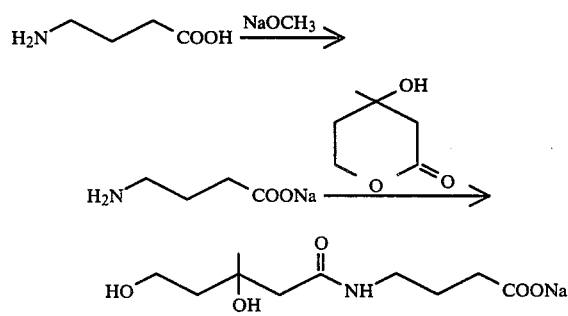

Sodium methoxide (0.54 g; 10 mmoles) and 1.03 g (10 mmoles) of gamma-aminobutyric acid were added to 10 ml of methanol. The mixture was stirred under reflux for 5 hours, and cooled to room temperature. Then, 1.3 g (10 mmoles) of beta-hydroxy-beta-methyl-delta-valerolactone was added. The mixture was stirred at room temperature (about 15° C.) for 12 hours. Methanol was distilled off under reduced pressure to give a slightly yellow viscous liquid. Analysis of this product by NMR spectroscopy in D$_2$O showed that it was sodium 4-(3,5-dihydroxy-3-methylpentylamide) butyrate having a purity of more than 95% containing small amounts of gamma-aminobutyric acid, beta-hydroxy-beta-methyl-delta-valerolactone and methanol. The product was purified by GPC in the same way as in Example 1. The results of NMR analysis and IR analysis of the purified product were substantially the same as those obtained in Example 1. The results of elemental analysis were as follows:
Found (%): C, 46.91; H, 7.40.
Calculated (%): C, 47.05; H, 7.11.

EXAMPLE 4

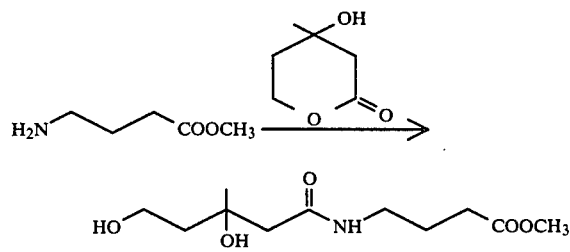

2.34 g (20 mmoles) of methyl gamma-aminobutyrate and 2.60 g (20 mmoles) of beta-hydroxy-beta-methyl-delta-valerolactone were dissolved in 50 ml of ethanol. The resulting mixture was stirred at room temperature (about 15° C.) for 15 hours. Ethanol was distilled off under reduced pressure to give 4.97 g of brown oil. This oil was purified by silica gel column chromatography [developing solvent: ethyl acetate:methanol=99:1 (by volume)] to give 4.69 g of a colorless liquid. The liquid was determined by NMR spectroscopy and infrared spectroscopy to be methyl 4-(3,5-dihydroxy-3-methyl-pentylamide) butyrate.

NMR ($\delta^{ppm}_{D_2O}$): 1.28 (s, 3H) ... (g)

1.81 (m, 4H) ... (b) + (e)
2.43 (s, 2H)

superimposed on t, 2H) ... (d) + (a)

3.23 (t. 2H) ... (c)

3.72 (s, 3H) ... (f)

3.75 (t, 3H) ... (h)

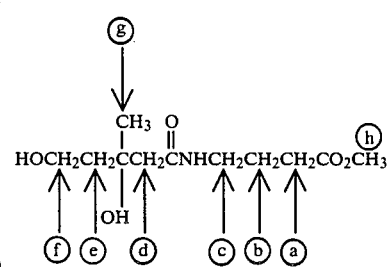

IR (cm$^{-1}$): 3300 (—OH), 1720 ($\overset{O}{\overset{\|}{C}}$OCH$_3$)

1630 (—$\overset{O}{\overset{\|}{C}}$—NH—), 1540 ( $\diagdown$NH of amide group $\diagup$ )

FORMULATION EXAMPLE 1

Injectable preparation

Calcium 4-(3,5-dihydroxy-3-methylpentylamide) butyrate (30 mg) was dissolved in 3 ml of normal saline solution and filled aseptically into a 3 ml. ampoule. The ampoule was sealed up by melting and heat-sterilized to form an injectable preparation which was aseptic and did not contain a pyrogenic substance.

FORMULATION EXAMPLE 2

| Tablets | |
|---|---|
| Calcium 4-(3,5-dihydroxy-3-methylpentylamide)butyrate | 30 mg |
| Lactose | 100 mg |
| Hydroxypropyl cellulose | 2.5 mg |
| Crystalline cellulose | 20 mg |
| Talc | 1.7 mg |
| Magnesium stearate | 1.8 mg |

The above ingredients were mixed and directly tableted by a tableting machine to form tablets each weighing 150 mg.

| Tablets | |
|---|---|
| Calcium 4-(3,5-dihydroxy-3-methylpentylamide)butyrate | 100 g |
| Corn starch | 145 g |
| Carboxy cellulose | 40 g |
| Polyvinyl pyrrolidone | 9 g |
| Calcium stearate | 6 g |
| Total amount | 300 g |

Tablets each weighing 300 mg were prepared from the above ingredients in a customary manner. One tablet contained 100 mg of the active compound.

FORMULATION EXAMPLE 4

| Powder and capsules | |
|---|---|
| Calcium 4-(3,5-dihydroxy-3-methylpentylamide)butyrate | 100 g |
| Crystalline cellulose | 200 g |
| Total amount | 300 g |

The above ingredients in powder form were mixed to form a powder. The powder was filled in No. 3 hard capsules to form capsules.

What is claimed is:

1. A compound which is calcium 4-(3,5-dihydroxy-3-methylpentylamide) butyrate.

2. A pharmaceutical composition for the prevention or treatment of an impediment of memory induced by derangement in the regulation of metabolism in the brain, which comprises an amount, effective for the prevention or treatment of said impediment, of calcium 4-(3,5-dihydroxy-3-methylpentylamide) butyrate and a pharmaceutically acceptable diluent or carrier.

3. A method for preventing or treating an impediment of memory induced by derangement in the regulation of metabolism in the brain, in a human suffering from said impediment, which comprises administering an effective amount of 4-(3,5-dihydroxy-3-methylpentylamide) butyric acid or a pharmaceutically acceptable salt or lower alkyl ester thereof to said human.

* * * * *